(12) United States Patent
Albers et al.

(10) Patent No.: US 12,415,871 B2
(45) Date of Patent: Sep. 16, 2025

(54) METHOD OF PRODUCING A PECTIC POLYSACCHARIDE ISOLATE ENRICHED IN RHAMNOGALACTURONAN-I

(71) Applicant: NutriLeads B.V., Wageningen (NL)

(72) Inventors: Ruud Albers, Rockanje (NL); Maria Tzoumaki, Wageningen (NL)

(73) Assignee: NutriLeads B.V., Wageningen (NL)

( * ) Notice: Subject to any disclaimer, the term of this patent is extended or adjusted under 35 U.S.C. 154(b) by 712 days.

(21) Appl. No.: 16/855,562

(22) Filed: Apr. 22, 2020

(65) Prior Publication Data

US 2020/0247912 A1   Aug. 6, 2020

Related U.S. Application Data

(63) Continuation of application No. PCT/EP2018/079058, filed on Oct. 23, 2018.

(30) Foreign Application Priority Data

Oct. 23, 2017  (EP) .................................... 17197706

(51) Int. Cl.
C08B 37/00     (2006.01)
C12P 19/00     (2006.01)

(52) U.S. Cl.
CPC .......... *C08B 37/0045* (2013.01); *C12P 19/00* (2013.01); *C12Y 302/01015* (2013.01); *C12Y 302/01067* (2013.01); *C12Y 302/01082* (2013.01); *C12Y 402/02002* (2013.01); *C12Y 402/0201* (2013.01)

(58) Field of Classification Search
None
See application file for complete search history.

(56) References Cited

U.S. PATENT DOCUMENTS

| | | | |
|---|---|---|---|
| 10,537,597 B2 | 1/2020 | O'Mahony et al. | |
| 2002/0022601 A1 | 2/2002 | Konno et al. | |
| 2004/0072791 A1 | 4/2004 | Kunz et al. | |
| 2004/0161422 A1 | 8/2004 | Ranganathan | |
| 2009/0139134 A1* | 6/2009 | Yoshikuni ............... | C12P 5/026 435/157 |
| 2010/0047209 A1 | 2/2010 | Stanton et al. | |
| 2011/0112048 A1 | 5/2011 | Cox et al. | |
| 2013/0137757 A1 | 5/2013 | Koide | |
| 2014/0275233 A1 | 9/2014 | Heiman | |
| 2014/0288021 A1 | 9/2014 | Freitas et al. | |
| 2016/0151485 A1 | 6/2016 | Albers et al. | |
| 2016/0250625 A1 | 9/2016 | Kanaya et al. | |
| 2018/0117099 A1 | 5/2018 | Chatila et al. | |

FOREIGN PATENT DOCUMENTS

| | | | | |
|---|---|---|---|---|
| CN | 102784193 A | | 11/2012 | |
| JP | 06256198 A | * | 9/1994 | |
| KR | 1020170053144 A | | 5/2017 | |
| WO | WO-01/76609 A1 | | 10/2001 | |
| WO | WO-02082923 A1 | * | 10/2002 | ........... A23L 1/0524 |
| WO | WO-2004/084652 A1 | | 10/2004 | |
| WO | WO-2005/095463 A1 | | 10/2005 | |
| WO | WO-2011/069781 A1 | | 6/2011 | |
| WO | WO-2011/136634 A1 | | 11/2011 | |
| WO | WO-2012/148277 A1 | | 11/2012 | |
| WO | WO-2015/192247 A1 | | 12/2015 | |
| WO | WO-2016/132130 A1 | | 8/2016 | |

OTHER PUBLICATIONS

Kegg ("Enzyme: 3.1.1.11." available at https://www.genome.jp/dbget-bin/www_bget?ec:3.1.1.11, accessed on Feb. 18, 2023) (Year: 2023).*
Bhushan ("Processing of Apple Pomace for Bioactive Molecules", Critical Review in Biotechnology, (2008), 28:285-296). (Year: 2008).*
Hotchkiss ("Carrot rhamnogalacturonan I structure and composition changed during 2017 in California" Food Hydrocolloids, 2023, 137, 108411, 1-11). (Year: 2023).*
Broxterman Suzanne E et al: "Acetylated pectins in raw and heat processed carrots", Carbohydrate Polymers, vol. 177, Aug. 30, 2017 (Aug. 30, 2017), pp. 58-66, XP085205714, ISSN: 0144-8617, DOI: 10.1016/J.CARBPOL.2017.08.118.
International Search Report mailed Jan. 4, 2019 received in corresponding International Application No. PCT/EP2018/079055, 5 pages.

(Continued)

*Primary Examiner* — Robert J Yamasaki
*Assistant Examiner* — Charles Z Constantine
(74) *Attorney, Agent, or Firm* — Foley & Lardner LLP

(57) ABSTRACT

The invention provides a method of producing a hydrolysed pectic polysaccharide isolate that is enriched in rhamnogalacturonan-I, said method comprising the steps of:
providing a pectin-rich substrate that has been obtained from plant material without the use of organic solvent, said pectin-rich substrate containing at least 3% by weight of dry matter of pectic polysaccharides;
subjecting the pectin-rich substrate to enzymatic treatment to partially hydrolyse the pectic polysaccharides, said treatment enzymatic treatment comprising the use of one or more pectinases selected from pectin lyase (EC4.2.2.10), pectate lyase (EC 4.2.2.2), rhamnogalacturonan galacturonohydrolase (EC 3.2.1.173), endo-polygalacturonase (EC 3.2.1.15), exopolygalacturonase (EC 3.2.1.67 and EC 3.2.1.82);
subjecting the partially hydrolysed pectic polysaccharides to ultrafiltration using an ultrafiltration membrane having a molecular weight cut-off in the range of 5 to 100 kDa; and
recovering the ultrafiltration retentate.
The present invention further relates to the hydrolysed pectic polysaccharide isolate obtained by the present method and to a process of preparing a product selected from a nutritional formulation, a food product, a dietary supplement, a beverage or a pharmaceutical product, said process comprising addition of the aforementioned hydrolysed pectic polysaccharide isolate.

18 Claims, 3 Drawing Sheets

(56) References Cited

OTHER PUBLICATIONS

International Search Report mailed Jan. 4, 2019 received in corresponding International Application No. PCT/EP2018/079058, 5 pages.
Kirtschev[Kirchev] N A et al: "Pectins of some carrot (*Daucus carota*) varieties. (translated) TIOL—Ueber Pektinstoffeeiniger Vertreter der Art Daucus Carota.". Zeitschrift Fuer Lebensmittel-Untersuchung Und -Forschung, vol. 170, No. 1, 1980, pp. 31-33, XP002776946.
Merve Kaya et al: "Characterization of citrus pectin samples extracted under different conditions: influence of acid type and pH of extraction", Annals of Botany., vol. 114, No. 6, Jul. 31, 2014 (Jul. 31, 2014), pp. 1319-1326, XP055535664, GB ISSN: 0305-7364, DOI: 10.1093/aob/mcu150.
Morris GA et al: "Physical characterisation of the rhamnogalacturonan and homogalacturonan fractions of sugar beet (*Beta vulgaris*) pectin", Carbohydrate Polymers, Applied Science Publishers, Ltd. Barking, GB, vol. 82, No. 4, Nov. 11, 2010 (Nov. 11, 2010), pp. 1161-1167, XP027266305, ISSN: 0144-8617 [retrieved on Sep. 7, 2010] paragraphs [02.2], [03.5]; example fig. 1.
Nastaran Khodaei et al: "Extraction and structural characterisation of rhamnogalacturonan I-type pectic polysaccharides from potato cell wall", Food Chemistry, vol. 139, No. 1-4, Feb. 10, 2013 (Feb. 10, 2013), pp. 617-623, XP55244701, NL ISSN: 0308-8146, DOI: 10.1016/j.foodchem.2013.01.110 paragraphs [02.1], [2.2.1], [2.2.2], [03.1], [03.2], [03.3], [03.4], [0004].
Park Hye-Ryung et al: "Structural 1-12, elucidation of anti-metastatic 14-20 rhamnogalacturonan I I from the pectinase digest of citrus peels (*Citrus unshiu*)", International Journal of Biological Macromolecules, ELS EV I ER BV, NL, vol. 94, Sep. 29, 2016 (Sep. 29, 2016), pp. 161-169, XP029818798, ISSN: 0141-8130, DOI: 10.1016/J.IJBIOMAC.2016.09.100 paragraphs [0001], [02.1], [02.2], [03.1]; figure 1.
Ridley B L et al: "Pectins: structure, biosynthesis, and oligogalacturonide-related signaling", Phytochemi, Pergamon Press, GB, vol. 57, No. 6, Jul. 1, 2001 (Jul. 1, 2001), pp. 929-967, XP004245805, ISSN: 0031-9422, DOI: 10.1016/S0031-9422(01)00113-3.
"Common Cold", Mayo Clinic; available at https://www.mayoclinic.org/diseases-conditionals/common-cold/symptoms-causes/syc-20351605; last accessed Jun. 2022.
"Prevent" definition, WordNet Search 3.1; available at wordnetweb.princeton.edu/perl/webwn; last accessed Jan. 2021 (1 page).
Alaa Abdul Aziz: "The effect of the Capsicum annuum in the diet of broilers on the isolation and shedding rate of *Salmonella paratyphoid*." Al-Qadssiya University, Vet. Med. Coll. Kufa Journal For Veterinary Medical sciences, vol.(1), No. (1, 2010.
Anne Petersen et al: "Some putative prebiotics increase the severity of *Salmonella enterica* serovar Typhimurium infection in mice", BMC Microbiology 2009, 9:245, Nov. 30, 2009.
Babbar et al., "Pectic oligosaccharides from agricultural by-products: production, characterization and health benefits", Critical Reviews in Biotechnology, vol. 36, No. 4, 2015, pp. 594-606.
Bonnin et al., "Pectin-modifying enzymes and pectin-derived materials: applications and impacts", Appl Microbiol Biotechnol (2014) 98: 519-532 (14 pages).
Bryony N. Parsons et al: "Dietary Supplementation with Soluble Plantain Non-Starch Polysaccharides Inhibits Intestinal Invasion of *Salmonella typhimurium* in the Chicken". PLOS ONE, vol. 9, No. 2, Feb. 3, 2014 (Feb. 3, 2014), p. e87658, XP055496849, DOI: 10.1371/journal.pone.0087658 the whole document.
Chatterjee et al., "Effect of Fruit Pectin on Growth of Lactic Acid Bacteria", Journal of Probiotics & Health, vol. 4, No. 2, 2016 (6 pages).
De Weirdt et al., "Human faecal microbiota display variable patterns of glycerol metabolism", FEMS Microbiology Ecology, vol. 74, 2010, pp. 601-611 (11 pages).
Edgar, "Search and clustering orders of magnitude faster than BLAST", Bioinformatics, vol. 26, No. 19, 2010, pp. 2460-2461 (2 pages).
Ferrere, G. et al., Journal of Hepatology, "Fecal microbiota manipulation prevents dysbiosis and alcohol-induced liver injury in mice", 2017, vol. 66, pp. 806-815 (Year: 2017).
Gomez et al. "Prebiotic potential of pectins and pectic oligosaccharides derived from lemon peel wastes and sugar beet pulp: A comparative evaluation", Journal of Functional Foods, vol. 20, 2016, pp. 108-121 (14 pages).
Gregory et al. "QIIME allows analysis of high-throughput community sequencing data" Nature Methods, vol. 7, No. 5, 2010, pp. 335-336 (4 pages).
International Search Report issued for PCT Appl. Ser. No. PCT/EP2018/074127 dated Dec. 11, 2018 (4 pages).
Khodaei et al., "Enzymatic extraction of galactan-rich rhamnogalacturonan I from potato cell wall by-product", LWT—Food Science and Technology, vol. 57, 2014, pp. 207-216 (10 pages).
Kim et al., "Effect of arabinoxylan- and rhamnogalacturonan I-rich polysaccharides isolated from young barley leaf on intestinal immunostimulatory activity", Journal of Functional Foods, vol. 35, 2017, pp. 384-390 (7 pages).
Looijer-van Langen, M. et al., Inflamm Bowel Dis., "Prebiotics in Chronic Intestinal Inflammation", 2009, vol. 15, pp. 454-462 (Year:2009).
Reeves, et al. "AIN-93 Purified Diets for Laboratory Rodents: Final Report of the American Institute of Nutrition Ad Hoc Writing Committee on the Reformulation of the AIN-76A Rodent Diet" Journal of Nutrition, vol. 123, No. 11, 1993, pp. 1939-1951 (15 pages).
Wright et al., "Multidrug-resistant *Salmonella typhimurium* in Four Animal Facilities", Emerging Infectious Diseases, 2005, 11(8), pp. 1235-1241.
Ferreira-Lazarte et al., "In vitro fermentation properties of pectins and enzymatic-modified pectins obtained from different renewable bioresources", Carbohydrate Polymers, Elsevier, vol. 199, Jul. 21, 2018, pp. 482-491.
International Search Report and Written Opinion for PCT Appl. Ser. No. PCT/NL2017/050807 dated Aug. 13, 2018 (10 pages).
Lau et al., "Structure of the Backbone of Rhamnogalacturonan I, A Petic Polysaccharide in the Primary Cell Walls of Plants", Carbohydrate Research, vol. 137, Elsevier Science Publishers B.V., Amsterdam, Jun. 25, 1984, pp. 111-125.
Jiao et al., "Chemical and antihyperglycemic activity changes of ginseng pectin induced by heat processing", Carbohydrate Polymers, Elsevier, vol. 114, Aug. 20, 2014, pp. 567-573.

* cited by examiner

METHOD OF PRODUCING A PECTIC POLYSACCHARIDE ISOLATE ENRICHED IN RHAMNOGALACTURONAN-I

CROSS-REFERENCE TO RELATED APPLICATIONS

This application is a continuation of International Application No. PCT/EP2018/079058, filed Oct. 23, 2018, and claims the benefit of priority to European application No. 17197706.9, filed Oct. 23, 2017, International Application No. PCT/NL2017/050807 filed Dec. 4, 2017, and International Application No. PCT/EP2018/074127 filed Sep. 7, 2018, the entire contents of which are hereby incorporated by reference herein in their entireties.

TECHNICAL FIELD OF THE INVENTION

The present invention relates to a method of producing a pectic polysaccharide isolate that is enriched in rhamnogalacturonan-I (RG-I) polysaccharide. More particularly, the invention relates to a method of producing such a polysaccharide isolate by enzymatic hydrolysis of a pectin-rich substrate that has been obtained from plant material without the use of organic solvent and that contains a significant amount of RG-I polysaccharide, followed by ultrafiltration and recovery of the retentate.

BACKGROUND OF THE INVENTION

Pectin is a structural hetero polysaccharide that is present in the primary cell walls of terrestrial plants. Pectic polysaccharide composition and fine structure vary widely depending on the plant source and the extraction conditions applied. The biological activity of the pectic polysaccharide is highly dependent on its fine structure.

Pectic polysaccharides are a heterogeneous group of polysaccharides comprising varying amounts of the following polysaccharide components:
(i) homogalacturonan (HG),
(ii) xylogalacturonan (XG),
(iii) apiogalacturonan (AG)
(iv) rhamnogalacturonan-I (RG-I), and
(v) rhamnogalacturonan-II (RG-II).

FIG. 1 provides a schematic representation of the structure of pectic polysaccharides, including the aforementioned 4 polysaccharide components. It is noted that the polysaccharide components AG, XG and RG-II typically represent only a minor fraction of pectic polysaccharides.

The polysaccharide components HG, XG and RG-II each comprise a backbone that consists of a linear chain of α-(1-4)-linked D-galacturonic acid monosaccharide units.

Only RG-I comprises a backbone that consists of a linear chain of the repeating disaccharide units: 4)-α-D-galacturonic acid-(1,2)-α-L-rhamnose-(1. A schematic representation of the structure of RG-I is shown in FIG. 2.

The homogalacturonan domain can have a length of up to about 100 consecutive D-GalA residues. The RG-I domain containing the side chains is usually called the 'ramified region' or 'hairy region', while the homogalacturonan domain (between two RG-I domains) is not typically substituted with oligosaccharides.

The GalA residues in RG-I are linked to the Rha residues via the 1 and 4 positions, while the Rha residue is linked to the GalA residue via the anomeric and 2-OH positions. In general about 20-80% of the Rha residues is branched at the 4-OH position (depending on the plant source and the method of isolation), with neutral and acidic side chains. These side chains consist mainly of Ara and Gal residues linked in various manners, constituting polymers known as arabinogalactan I (AG-I) and/or AG-II. AG I is composed of a beta-(1,4)-linked D-Gal backbone with substitutions at 3-OH of alpha-L-arabinosyl groups; the Gal backbone can have interspacing alpha(1,5)-L-Ara units. AG-II consists of highly ramified galactan with predominantly interior beta(1, 3)-linked D-Gal with substitutions of short (1,6)-linked chains exteriorly. The latter has further attachments of (1,3)- and/or alpha(1,5)-linked L-Ara. The oligosaccharide side chains may be linear or branched, and some of these side chains may be terminated with alpha-L-fucosides, beta-D-glucuronides, and 4-O-methyl beta-D-glucuronyl residues.

Khodaei and Karboune ("Extraction and structural characterisation of rhamnogalacturonan I-type pectic polysaccharides from potato cell wall". *Food Chemistry*, 1:39 (2013), p. 617-623) described the extraction of galactan-rich rhamnogalacturonan I (RG-I) type pectic polysaccharides using alkaline (NaOH and KOH) and enzymatic (endopolygalacturonase from *Aspergillus niger*) methods.

Khodaei and Karboune ("Enzymatic extraction of galactan-rich rhamnogalacturonan I from potato cell wall by-product". LWT—*Food Science and Technology*, 57 (2014), p. 207-216) further investigated the effects of varying parameters in the enzymatic extraction of galactan-rich rhamnogalacturonan I (RG I) using endo-polygalacturonase from *Aspergillus niger*.

WO 2015/192247 describes a process of isolating non-digestible oligosaccharides from potato pulp by extracting rhamnogalacturonan content from the potato pulp, digesting the extracted rhamnogalacturonan content with a multi-enzymatic mixture to yield the non-digestible oligosaccharides from the extracted rhamnogalacturonan content; and isolating the non-digestible oligosaccharides.

WO 2016/132130 describes a process for the preparation of a fragment of RG-I from potato pulp and its use to provide immunomodulatory activity to a subject. The process comprises the steps of:
providing RG-I obtained from the enzymatic extraction of potato;
preparing a fragment of said RG-I, the fragment having an average molecular weight in the range 5 kDa to 30 kDa, by selective depolymerisation of said RG-I to provide the fragment wherein the fragment has a monosaccharide composition comprising:
Arabinose 7-13%,
Rhamnose 5-10%,
Xylose 0-1%,
Galacturonic acid 20-40%, and
Galactose 35-60%.

CN 102784193 A describes a method of isolating polysaccharides from *Hedysarum polybotrys*.

KR 2017/053144 A describes the extraction of a polysaccharide fraction from barley leaves. The polysaccharide fraction is described to present immunity function promotion activity.

SUMMARY OF THE INVENTION

The inventors have discovered that a polysaccharide isolate enriched in rhamnogalacturonan-I (RG-I) polysaccharide with high biological functionality can be obtained by a method comprising:
subjecting a pectin-rich substrate that has been obtained from plant material without the use of organic solvent and that contains a significant amount of RG-I polysaccharide to enzymatic hydrolysis to partially hydrolyse the RG-I polysaccharide;

subjecting the partially hydrolysed RG-I polysaccharide to ultrafiltration using an ultrafiltration membrane having a cut-off in the range of 5 to 100 kDa;

and recovering the ultrafiltration retentate.

The enzymatic hydrolysis is carried out with the help of one or more pectinases selected from pectin lyase (EC4.2.2.10), pectate lyase (EC 4.2.2.2), rhamnogalacturonan galacturonohydrolase (EC 3.2.1.173), endo-polygalacturonase (EC 3.2.1.15), exopolygalacturonase (EC 3.2.1.67 and EC 3.2.1.82).

Thus, a first aspect of the present invention relates to providing a method of producing a hydrolysed pectic polysaccharide isolate that is enriched in rhamnogalacturonan-I, said method comprising the steps of:

providing a pectin-rich substrate that has been obtained from plant material without the use of organic solvent, said pectin-rich substrate containing at least 3% by weight of dry matter of pectic polysaccharides having a backbone consisting of galacturonic acid residues and rhamnose residues, the rhamnose residues being contained in a backbone consisting of galacturonic acid residues and rhamnose residues, said rhamnose residues being contained in alpha(1→4)-galacturonic-alpha(1→2)-rhamnose residues;

subjecting the pectin-rich substrate to enzymatic treatment to partially hydrolyse the pectic polysaccharides, said treatment enzymatic treatment comprising the use of one or more pectinases selected from pectin lyase (EC4.2.2.10), pectate lyase (EC 4.2.2.2), rhamnogalacturonan galacturonohydrolase (EC 3.2.1.173), endo-polygalacturonase (EC 3.2.1.15), exopolygalacturonase (EC 3.2.1.67 and EC 3.2.1.82);

subjecting the partially hydrolysed pectic polysaccharides to ultrafiltration using an ultrafiltration membrane having a molecular weight cut-off in the range of 5 to 100 kDa; and recovering the ultrafiltration retentate.

The inventors have found that enzymatic partial hydrolysis of the pectic polysaccharides using one or more of the aforementioned pectinases followed by the removal of small molecular components, including small molecules produced during hydrolysis, yields a hydrolysed pectic polysaccharide isolate that exhibits exceptionally high biological functionality.

Although the inventors do not wish to be bound by theory, it is believed that this high biological functionality is achieved by removing at least part of the homogalacturonan domains of the pectic polysaccharides contained in the substrate, and by removing inactive components, such as cellulose and hemicellulose. The removal of the homogalacturonan domains alters the physicochemical properties of the pectic polysaccharides, resulting in three-dimensional configurations of the molecule that can interact more effectively with so-called pattern recognition receptors in the intestinal tract and on human Peripheral Blood Mononuclear Cells. Removal of homogalacturonan domains from the pectic polysaccharides increases the content of RG-I domains. It is believed that interaction of RG-I polysaccharide domains with pattern recognition receptors expressed on intestinal cells and other immunologically active cells can modulate their functional responsiveness, which through production of mediators and recirculation of immunologically active cells can improve resistance to infections in the intestinal tract as well as at other sites in the body including the oral cavity, the respiratory tract, the urinary tract, the vagina and the skin.

The present method further offers the advantage that the highly active hydrolysed pectic polysaccharide is obtained from a pectin-rich substrate that has been produced without the use of organic solvent. Thus, unlike some prior art methods that utilize organic solvent precipitation to aid the isolation of pectic polysaccharides, the present method employs a pectin-rich substrate that has not been contacted with organic solvent and the further processing of this substrate in accordance with the present method does not require the use of organic solvent.

The present invention further relates to the hydrolysed pectic polysaccharide isolate obtained by the present method and to a process of preparing a product selected from a nutritional formulation, a food product, a dietary supplement, a beverage or a pharmaceutical product, said process comprising addition of the aforementioned hydrolysed pectic polysaccharide isolate.

DETAILED DESCRIPTION OF THE INVENTION

Figure 1:
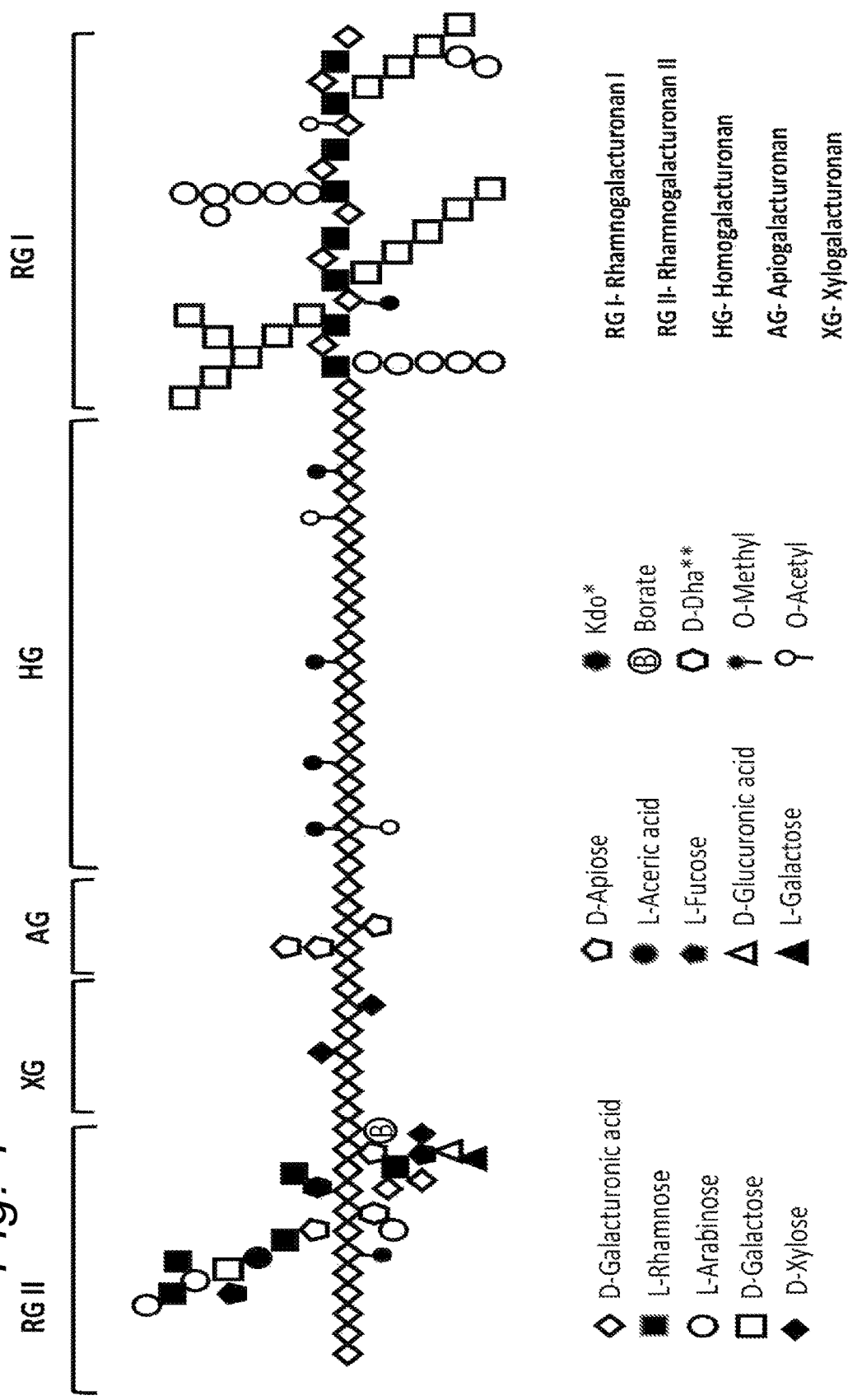
FIG. 1 provides a schematic representation of the structure of pectic polysaccharides, including the aforementioned 4 polysaccharide components.
Figure 2:
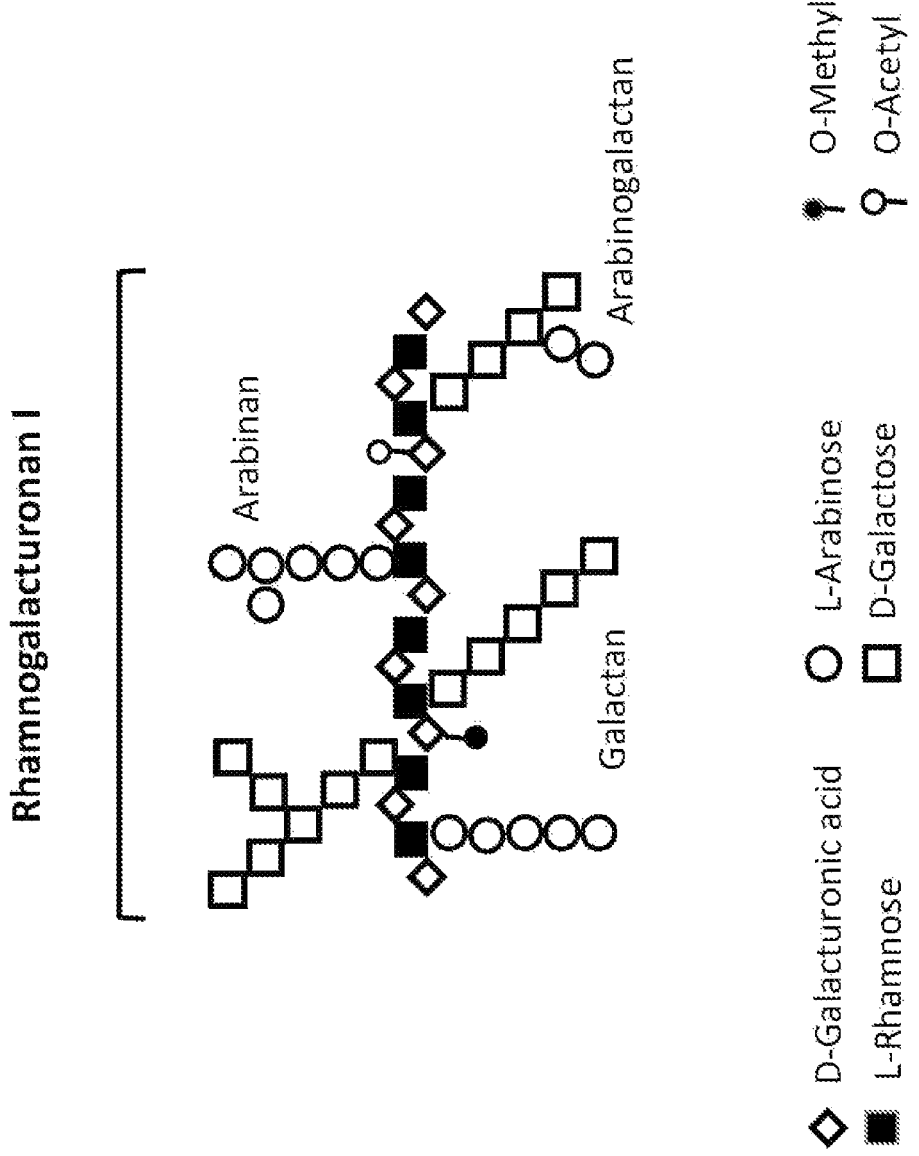
FIG. 2 provides a schematic representation of the structure of RG-I comprising a backbone that consists of a linear chain of the repeating disaccharide units: 4)-α-D-galacturonic acid-(1,2)-α-L-rhamnose-(1.

Accordingly, a first aspect of the invention relates to a method of producing a hydrolysed pectic polysaccharide isolate that is enriched in rhamnogalacturonan-I, said method comprising the steps of:

providing a pectin-rich substrate that has been obtained from plant material without the use of organic solvent, said pectin-rich substrate containing at least 3% by weight of dry matter of pectic polysaccharides having a backbone consisting of galacturonic acid residues and rhamnose residues, the rhamnose residues being contained in a backbone consisting of galacturonic acid residues and rhamnose residues, said rhamnose residues being contained in alpha(1→4)-galacturonic-alpha(1→2)-rhamnose residues;

subjecting the pectin-rich substrate to enzymatic treatment to partially hydrolyse the pectic polysaccharides, said treatment enzymatic treatment comprising the use of one or more pectinases selected from pectin lyase (EC4.2.2.10), pectate lyase (EC 4.2.2.2), rhamnogalacturonan galacturonohydrolase (EC 3.2.1.173), endo-polygalacturonase (EC 3.2.1.15), exopolygalacturonase (EC 3.2.1.67 and EC 3.2.1.82);

subjecting the partially hydrolysed pectic polysaccharides to ultrafiltration using an ultrafiltration membrane having a molecular weight cut-off in the range of 5 to 100 kDa; and recovering the ultrafiltration retentate.

The pectin-rich substrate that is used in the present method has been obtained from plant material without the use of organic solvent, meaning that this substrate was obtained from plant material without that plant material having been brought in contact with organic solvent. Thus, the pectin-rich substrate is not obtained through extraction or precipitation with organic solvent.

As used herein, the terms "backbone chain" and "backbone" are synonyms.

The term "saccharide" as used herein encompasses mono-, di-, oligo- and polysaccharides.

The term "oligosaccharide" as used herein refers to a saccharide polymer containing 3-10 monosaccharide residues.

The term "polysaccharide" as user herein, unless indicated otherwise, refers to a saccharide polymer containing at least 11 monosaccharide residues.

The term "pectic polysaccharide" as used herein refers to optionally branched polysaccharides having a molecular weight of at least 10 kDa and comprising a backbone that consists of galacturonic acid residues and rhamnose residues, said rhamnose residues being contained in alpha (1→4)-galacturonic-alpha(1→2)-rhamnose residues. The term "pectic polysaccharide" as used herein, unless indicated otherwise, also encompasses hydrolysed pectic polysaccharides having a molecular weight of at least 10 kDa.

The term "branched polysaccharide" as used herein refers to a polysaccharide comprising a linear backbone chain of monosaccharide units bound together by glycosidic linkages, wherein at least one of the monosaccharide units within the backbone chain carries a sidechain of one or more glycosidically linked monosaccharide units.

The term "stretch" as used herein refers to a sequence of two glycosidically linked monosaccharide units within the backbone of a polysaccharide, excluding any sidechains that are attached thereto.

The term "domain" as used herein refers to a stretch plus any sidechains that are attached to said stretch.

The term "rhamnogalacturonan-I stretch" or "RG-I stretch" refers to a stretch consisting of galacturonic acid (GalA) and rhamnose (Rha) pairs, wherein the GalA residues are linked to the Rha residues via the 1 and 4 positions, while the Rha residues are linked to the GalA residue via the anomeric and 2-OH positions, i.e. alternating alpha(1→4)-galacturonic-alpha(1→2)-rhamnose residues. The RG-I domain can comprise side chains such as, for example galactan, arabinan and arabinogalactan side chains.

The term "rhamnogalacturonan-I polysaccharide" or "RG-I polysaccharide" refers to optionally branched pectic polysaccharides that comprise a backbone that contains one or more rhamnogalacturonan-I stretches.

The term "alpha(I,4)-linked galacturonic acid stretch" refers to a stretch consisting of alpha(1→4)-galacturonic residues.

Besides RG-I domains, the hydrolysed pectic polysaccharide isolate obtained by the method of the present invention may contain one or more of the following domains:
homogalacturonan (HG),
xylogalacturonan (XG),
apiogalacturonan (AG)
rhamnogalacturonan-II (RG-II).

The domains XG, AG and RG-II typically represent only a minor fraction of the RG-I polysaccharides.

The HG domains, XG domains, AG and RG-II domains that are optionally present in the RG-I polysaccharides of the present invention comprise a backbone that consists of a linear chain of two or more α-(1-4)-linked D-galacturonic acids.

HG domains do not contain any sidechains. The carboxyl groups of galacturonic acid residues within the backbone of HG domains may be esterified. Esterified galacturonic acid may occur in the form of the methyl ester or acetyl ester.

The backbone of XG domains contains one or more sidechains in the form of D-xylose.

The backbone of AG domains contains one or more sidechains that are composed of one or more D-apiose residues.

The backbone of RG-II contains one or more side chains that are not exclusively composed of D-xylose or D-apiose. The carboxyl groups of galacturonic acid residues within the backbone of RG-II domains may be esterified. Esterified galacturonic acid may occur in the form of the methyl ester or acetyl ester.

The terminology "degree of acetylation" refers to the number of acetyl residues per galacturonic acid residue, expressed as a percentage.

The terminology "degree of methylation" refers to the number of methyl residues per galacturonic acid residue, expressed as a percentage.

The concentration of different polysaccharides and their monosaccharide composition can be determined by analytical techniques known to the skilled person. After methanolysis, the monosaccharide composition can suitably be determined by High Performance Anion Exchange Chromatography combined with Pulse Amperometric Detection (HPAEC-PAD).

The molecular size distribution can be determined by High Performance Size-Exclusion Chromatography using refractive index (RI) detection (concentration), light scattering detection (molecular mass detection), UV detection (indicative for presence of proteins) and differential pressure detection (intrinsic viscosity detection).

The above mentioned analytical methods are described in: Analytical Biochemistry Vol. 207, Issue 1, 1992, pg 176 (for methanolysis and neutral sugar analysis) and in Mol. Nutr. Food Res., Vol 61, Issue 1, 2017, 1600243 (for the galacturonic acid analysis and the molecular size distribution).

The term "pomace" or "cake" as used herein refers to the, optionally dried, residue of fruit, vegetables or seeds that remains after pressing for juice or oil. The term "oil cake" refers to the cake that is obtained after removal of oil from seeds, fruit or vegetables.

All percentages mentioned herein, unless otherwise stated, refer to the percentage by weight.

The present method preferably does not employ any organic solvent. In other words, the pectin-rich substrate that has been obtained from plant material without the use of organic solvent is further processed (enzymatic treatment and ultrafiltration) to produce the desired hydrolysed pectic polysaccharide isolate, without the use of organic solvent.

The pectin-rich substrate used in the present method preferably contains at least 4% by weight of dry matter, more preferably at least 6% by weight of dry matter, even more preferably at least 8% by weight of dry matter of pectic polysaccharides.

The pectic polysaccharides in the pectin-rich substrate are preferably characterized by a mass weighted average molecular weight of at least 100 kDa, more preferably of at least 150 kDa, most preferably of at least 200 kDa, The pectic polysaccharides in the pectin-rich substrate typically have an average rhamnose content of at least 0.1 mol. %, more preferably of at least 0.5 mol. %, even more preferably at least 1 mol. % and most preferably at least 2 mol. %, calculated on the total monosaccharide composition of the pectic polysaccharides.

The pectin-rich substrate that is employed in the present method may be obtained from different crops. In a preferred embodiment, the pectin-rich substrate is obtained from one or more crops selected from fruit (including tomato), carrot, olive, peas, sugar beet, chicory, soy, sunflower, rapeseed and maize. More preferably, the pectin-rich substrate is obtained from one or more crops selected from apple, pear, citrus, carrot, sugar beet and chicory. Yet more preferably, the pectin-rich substrate is obtained from one or more crops selected from apple, pear, carrot and chicory. According to a particularly preferred embodiment, the pectin-rich substrate is obtained from carrot and/or apple.

Pectin-rich crop material may be used as such as the pectin-rich substrate in the present method. Such crop material should be comminuted to produce a pulp or a juice, in order to allow the pectinases to break down the pectic polysaccharides in the substrate. The comminuted crop material may be dried or concentrated before use in the present method.

Preferably, the pectin-rich substrate is obtained as a side stream from a production process that uses crop material as a starting material and wherein no organic solvents or chemical reactions are employed up to the stage of the process at which the side stream is generated. According to a particularly preferred embodiment of the present method, the pectin-rich substrate is selected from pomace, aqueous extract of pomace, oil cake, aqueous extract of oil cake, scrapings, skins, peels, pits, seeds and combinations thereof. Most preferably, the pectin-rich substrate is selected from pomace, aqueous extract of pomace and combinations thereof.

The pectin-rich substrate that is employed in the present method may suitably be obtained by a procedure that includes milling, heating, microwaving, drying or alternative techniques that disrupt the cell wall structures to facilitate enzymatic hydrolysis of the pectic polysaccharides.

The pectin-rich substrate preferably has a water content of not more than 15 wt. %, more preferably of not more than 10 wt. % and most preferably of not more than 8 wt. %.

The pectin-rich substrate is preferably subjected to the enzymatic treatment in the form of an aqueous liquid containing the pectin-rich substrate and having a dry matter content of 0.5-40 wt. %, more preferably of 1-30 wt. %, even more preferably of 2-20 wt. %, most preferably 3-15 wt. %. This aqueous liquid may suitably be prepared by combining the pectin-rich substrate with water.

The pectin-rich substrate preferably constitutes at least 50 wt. %, more preferably at least 75 wt. % and most preferably at least 85 wt. % of the dry matter that is contained in the aqueous liquid that is subjected to enzymatic treatment.

The enzymatic treatment of the method according to the invention is preferably carried out at a pH in the range of 3.0 to 7.5, more preferably in the range of 4 to 7.5, even more preferably in the range of 4.5 to 7, most preferably in the range of 5 to 7.

The treatment used to partially hydrolyse the pectic polysaccharides preferably employs one or more pectinases selected from pectin lyase (EC 4.2.2.10), pectate lyase (EC 4.2.2.2), endopolygalacturonase (EC 3.2.1.15) and exopolygalacturonase (EC 3.2.1.67 and EC 3.2.1.82).

According to one preferred embodiment, the pectic polysaccharides are partially hydrolysed using one or more pectinases selected from endo-polygalacturonase (EC 3.2.1.15) and exopolygalacturonase (EC 3.2.1.67 and EC 3.2.1.82).

According to another preferred embodiment, the pectic polysaccharides are partially hydrolysed using one or more pectinases selected from pectin lyase (EC 4.2.2.10) and pectate lyase (EC 4.2.2.2). Hydrolysis of pectic polysaccharides by these lyases inevitably yields polysaccharide fragments that contain a terminal unsaturated non-reducing galacturonic acid residue.

The pectic polysaccharides are preferably hydrolysed in the present process using a combination of the aforementioned one or more pectinases and one or more pectinesterases (EC 3.1.1.11). The one or more pectinesterases may be employed prior to or simultaneous with the one or more pectinases. The combined use of pectinases and pectinesterases is particularly advantageous in case the pectinase employed is selected from endo-polygalacturonase, exo-polygalacturonase and combinations thereof. The combined use pecintases and pectinesterases typically yields partially hydrolysed pectic polysaccharides having a reduced degree of methylation and an increased acetylation/methylation ratio.

According to a particularly preferred embodiment, the pectin-rich substrate is subjected to enzymatic treatment comprising the use of one or more pectinesterases (EC 3.1.1.11) prior to or simultaneous with the partial hydrolysis using the one or more pectinases. Most preferably, the enzymatic treatment with pectinesterases and the enzymatic treatment with one or more pectinases are carried out simultaneously.

In the present method the pectin-rich substrate may suitably be treated with cellulase and/or hemicellulase (EC 3.2.1.4, EC 3.2.1.176, EC 3.2.1.203) prior to the enzymatic treatment with pectinase or as part of said treatment. Treatment with cellulase and/or hemicellulase breaks down plant cell walls in the substrate and thereby induces release of the pectins that are contained within these cell walls and thus makes these pectins more accessible for pectinases.

The enzymatic treatment of the pectin-rich substrate with one or more pectinases is preferably carried out at a temperature in the range of 15 to 70° C., more preferably of 25 to 55° C. The duration of the enzymatic treatment preferably is at least 10 minutes, more preferably 20 minutes to 3 hours.

The present method may suitably employ a pectin-rich substrate that contains a relatively high amount of more or less intact plant cell wall material. Typically, such a pectin-rich substrate contains at least 40% by weigh of dry matter of cellulose material selected from cellulose, hemi-cellulose and combinations thereof. Typically, a large fraction of the pectic polysaccharides in these substrates is water-insoluble, i.e. the pectic polysaccharides that are trapped in the cellulose/hemicellulose matrix of the plant cell wall (fragments). Preferably, at least 50 wt. % of the pectic polysaccharides present in the substrate does not dissolve in distilled water at 45° C. and pH 5.5 at a pectic polysaccharide concentration of 1 g/l.

In accordance with a particularly preferred embodiment of the present method, after enzymatic treatment and prior to ultrafiltration, water-soluble pectic polysaccharides are separated from non-water soluble solids by subjecting an aqueous liquid containing the partially hydrolysed pectic polysaccharides to solid-liquid separation. Examples of solid-liquid separation techniques that may be employed include sedimentation, decanting, centrifugation, hydrocyclones and/or filtration. This particular embodiment offers the advantage that a high yield of the desired pectic polysaccharides can be achieved.

In one embodiment of the present method, the pectin-rich substrate contains 10-80% by weight of dry matter of cell wall polysaccharides selected from pectins, cellulose, hemicellulose and combinations thereof. More preferably, the substrate contains 20-70% by weight of dry matter of the cell wall polysaccharides. Most preferably, the substrate contains 30-60% by weight of dry matter of the cell wall polysaccharides. Pomace is an example of a pectin-rich substrate that may be used in the present method and that contains a relatively high amount of cell wall polysaccharides.

Pomace typically contains 2-50% by weight of dry matter, preferably 5-40% by weight of dry matter, more preferably 10-30% by weight of dry matter, of carbohydrates having a molecular weight of less than 20 kDa.

The protein content of the pomace typical is in the range of 0-20% protein by weight of dry matter, more preferably 1-18% protein by weight of dry matter, even more preferably 2-16% protein by weight of dry matter.

In the embodiment of the present method in which the pectin-rich substrate is pomace or oil cake, preferably non-dissolved material (particle size >5 μm) is removed from the enzymatically treated pomace or the enzymatically treated oil cake prior to ultrafiltration. The non-dissolved material is preferably removed by means of solid-liquid separation, more preferably by decanting, centrifugation and/or filtration.

In another embodiment of the present method, the pectin-rich substrate is a pectin isolate containing at least 10% by weight of dry matter, preferably at least 20% by weight of dry matter, more preferably at least 40% by weight of dry matter, of the pectic polysaccharides, and less than 20% by weight of dry matter of cell wall polysaccharides selected from cellulose, hemicellulose and combinations thereof. More preferably, the pectin isolate contains cell wall polysaccharides in a concentration of less than 10% by weight of dry matter, even more preferably of less than 5% by weight of dry matter. Aqueous extracts of pomace and aqueous extracts of oil cake are examples of pectin isolates that may be employed in the present method as pectin-rich substrate.

Preferably, the aqueous pomace extract is obtained by a sequence of aqueous extraction steps, more preferably at least two aqueous extraction steps. Accordingly, the first extraction step preferably comprises mixing pomace with water followed by solid-liquid separation. The second step preferably comprises mixing the recovered solid fraction with water, followed by another solid-liquid separation. Suitable solid-liquid separation methods are, e.g., decanting, centrifugation and filtration.

Preferably, the aqueous extraction is carried out at a pH in the range of 2.0 to 8.5, more preferably at a pH in the range of 4.5 to 7.5, even more preferably at a pH in the range of 6.0 to 7.0.

In a particularly preferred embodiment of the present method, the partially hydrolysed pectic polysaccharides are subjected to ultrafiltration using an ultrafiltration membrane having a molecular weight cut-off in the range of 6-50 kDa, preferably in the range of 7-40 kDa, more preferably in the range of 8-30 kDa.

The recovered ultrafiltration retentate may suitably be dried using one or more drying techniques selected from spray drying, freeze drying, air drying, roller drying, flatbed drying, belt drying and drum drying.

Preferably, the recovered ultrafiltration retentate is dried to a water content of less than 15 wt. %, more preferably less than 13 wt. %, even more preferably less than 11 wt. %, and most preferably less than 9 wt. %.

The recovered ultrafiltration retentate preferably contains galacturonic acid residues and rhamnose residues in a molar ratio of not more than 6:1, more preferably of not more than 5:1, even more preferably of not more than 4:1, most preferably of not more than 3.5:1.

The pectic polysaccharides that are present in the recovered ultrafiltration retentate preferably have an average rhamnose content of at least 4%, more preferably 5-50%, even more preferably 6-45%, yet more preferably 6.5-40% and most preferably 7-30%, calculated on the total monosaccharide composition of the pectic polysaccharides.

The recovered ultrafiltration retentate preferably contains at least 5% by weight of dry matter, preferably at least 15% by weight of dry matter, more preferably at least 25% by weight of dry matter, most preferably at least 50% by weight of dry matter of pectic polysaccharides, said pectic polysaccharides having an average rhamnose content of at least 4 mol. %, calculated on the total monosaccharide composition of the pectic polysaccharides.

According to a further preferred embodiment, the pectic polysaccharides in the recovered retentate have a mass weighted average molecular weight of more than 20 kDa, more preferably of more than 30 kDa, even more preferably of more than 40 kDa, most preferably of more than 50 kDa.

The method of the present invention preferably yields a hydrolysed pectic polysaccharide isolate as specified below.

A second aspect of the invention relates to a hydrolysed pectic polysaccharide isolate obtained by the method according to the invention.

The hydrolysed pectic polysaccharide isolate typically has a dry matter content of at least 85 wt. %, more preferably of at least 90 wt. % and most preferably of at least 95 wt. %.

Preferably, the hydrolysed pectic polysaccharide isolate contains at least 10% by weight of dry mater, more preferably at least 20% by weight of dry matter, even more preferably at least 40% by weight of dry matter of pectic polysaccharides, said pectic polysaccharides having an average rhamnose content of at least 4 mol. %, calculated on the total monosaccharide composition of the pectic polysaccharides.

According to a particularly preferred embodiment, the hydrolysed pectic polysaccharides have a mass weighted average molecular weight of more than 20 kDa, more preferably of more than 30 kDa, even more preferably of more than 40 kDa, most preferably of more than 50 kDa.

In a particular embodiment, the hydrolysed pectic polysaccharide isolate contains less than 15 wt. %, less than 10 wt. %, more preferably less than 5 wt. %, most preferably less than 1 wt. % saccharides (polysaccharides, oligosaccharides, disaccharides and monosaccharides) having a molecular weight of less than 2.5 kDa.

Preferably, the hydrolysed pectic polysaccharide isolate contains less than 30 wt. %, more preferably less than 20 wt. %, even more preferably less than 10 wt. % organic substances having a molecular weight of less than 20 kDa.

Typically, the hydrolysed pectic polysaccharide isolate contains less than 15% by weight of dry matter, preferably less than 10% by weight of dry matter, more preferably less than 5% most preferably less than 1% by weight of dry matter of insoluble polysaccharides selected from cellulose, hemicellulose, lignin and starch.

The protein content of hydrolysed pectic polysaccharide isolate preferably does not exceed 15% by weight of dry matter, more preferably it is in the range of 0.5-10% by weight of dry matter and most preferably in the range of 1-5% by weight of dry matter.

Preferably, the hydrolysed pectic polysaccharide isolate contains at least 10% by weight of dry matter, preferably at least 20% by weight of dry matter, more preferably at least 30% by weight of dry matter of pectic polysaccharides, said pectic polysaccharides having an average rhamnose content of at least 5 mol. %, more preferably at least 6%, calculated on the total monosaccharide composition of the pectic polysaccharides.

Typically, the combination of galacturonic acid residues, rhamnose residues, arabinose residues and galactose residues constitutes at least 50 mol. % of the monosaccharide residues present in the saccharides that are contained in the hydrolysed pectic polysaccharide isolate. More preferably this combination constitutes at least 60 mol. %, even more preferably at least 65 mol. %, yet more preferably at least 70 mol. % and most preferably at least 75 mol. % of the monosaccharide residues in the saccharides that are contained in the hydrolysed pectic polysaccharide isolate.

In a particularly preferred embodiment of the hydrolysed pectic polysaccharide isolate, the combination of galacturonic acid residues and rhamnose residues represents at least 15 mol. %, more preferably 17-70 mol. %, most preferably 18-60 mol. % of the monosaccharide residues present in the saccharides that are contained in the hydrolysed pectic polysaccharide isolate.

Galacturonic acid residues and rhamnose residues are preferably present in the hydrolysed pectic polysaccharide isolate in a molar ratio of not more than 6:1, more preferably of not more than 5:1, even more preferably of not more than 4:1, most preferably of not more than 3.5:1.

Rhamnose residues typically represent 5-50%, more preferably 6-45% even more preferably 6.5-40% and most preferably 7-30% of all the monosaccharide residues contained in the pectic polysaccharides that are present in the hydrolysed pectic polysaccharide isolate.

Galacturonic acid residues typically represent 5-80%, more preferably 8-60% and most preferably 10-50% of all the monosaccharide residues contained in the pectic polysaccharides that are present in the hydrolysed pectic polysaccharides isolate.

The pectic polysaccharides in the isolate preferably have a mass weighted average molecular weight of not more than 800 kDa. More preferably, the pectic polysaccharides have a mass weighted average molecular weight between 22 kDa and 500 kDa, most preferably between 25 kDa and 250 kDa.

In a particular embodiment, the pectic polysaccharides in the isolate of the present invention preferably have an average degree of acetylation of at least 10%, more preferably of 20-110%, even preferably of 25-100% and most preferably of 30-80%.

In a further particular embodiment, the pectic polysaccharides in the isolate preferably have an average degree of methylation of not more than 60%, more preferably of not more than 50% and most preferably of 5-30%.

The backbone of the pectic polysaccharides in the isolate can comprise one or more side chains. These sidechains may contain residues of arabinose and/or galactose, and minor amounts of residues of the monomers fucose, glucose, glucuronic acid, xylose, and/or uronic acid. The one or more side chains preferably are selected from galactan side chains, arabinan side chains and arabinogalactan side chains.

The arabinan side chain comprises at least one or more alpha(1,5)-linked arabinose residues and is substituted at the 4-OH position of a rhamnose residues in the RG-I domain. The arabinan side chain may be linear or branched. In case the side chain is linear, the side chain consists of alpha(1, 5)-linked arabinose residues. In case the arabinan side chain is a branched side chain, one or more alpha-arabinose residues are linked to the 2-OH and/or 3-OH of alpha(1,5)-linked arabinoses.

The galactan side chain comprises at least one or more beta(1,4)-linked galactose residues and is substituted at the 4-OH position of a rhamnose residues in the RG-I domain.

The arabinogalactan side chain is substituted at the 4-OH position of a rhamnose residue in the RG-I domain and can be a type I arabinogalactan (AGI) or a type II arabinogalactan (AGII). AGI is composed of a (1→4)-β-D-Galp backbone on which substitutions by monomeric Galp units at the 0-6 or at the 0-3 position can occur. AGI is further substituted with α-L-Araf-p residues and/or with (1→5)-α-L-Araf short side chains. AGII is composed of α(1→3)-β-D-Galp backbone decorated with (1→6)-β-D-Galp secondary chains, which are arabinosylated.

Arabinose residues typically represent 0-50%, more preferably 3-48% and most preferably 5-46% of all the monosaccharide residues contained in the pectic polysaccharides that are present in the hydrolysed pectic polysaccharide isolate.

Galactose residues typically represent 0-50%, more preferably 3-35% and most preferably 5-25% of all the monosaccharide residues contained in the pectic polysaccharides that are present in the hydrolysed pectic polysaccharide isolate.

Galactose residues and rhamnose residues are preferably present in the pectic polysaccharides of the isolate in a molar ratio of less than 4:1, more preferably of less than 3:1, most preferably of less than 2:1.

A third aspect of the invention relates to a process of preparing a product selected from a nutritional formulation, a food product, a dietary supplement, a beverage or a pharmaceutical product, said process comprising addition of the hydrolysed pectic polysaccharide isolate according to the invention in a concentration of at least 0.1% by weight of the dry matter that is contained in the final product.

The hydrolysed pectic polysaccharide isolate is preferably added in a concentration of at least 0.2%, more preferably 0.3-95%, most preferably 1-80% by weight of the dry matter that is contained in the final product.

The product of the present invention may contain traces of one or more of the pectinases employed in the method of obtaining the hydrolysed pectic polysaccharide isolate. These pectinases may be present in the product in active and/or inactive form.

In a particularly preferred embodiment, the pectic polysaccharides of the hydrolysed pectic polysaccharide isolate represent at least 20 wt. %, more preferably at least 30 wt. %, even more preferably 60 wt. %, and most preferably at least 80 wt. % of the total amount of pectic polysaccharides present in the final product.

The invention is further illustrated by the following non-limiting examples.

EXAMPLES

Example 1

500 kg of dried carrot pomace (proteins 14-15%, carbohydrates 73% (sugars 16-18%, dietary fiber 55%), ash 3-4%, fat 6-7%) obtained from juice pressing were dispersed in 4500 L of 45° C. water, under stirring. 5 kg of enzyme preparation (Pectinex™ Ultra Mash, ex Novozymes, main activity pectin lyase and polygalacturonase) was added to the mixture (0.1% of the total 5000 L), followed by incubation at 45° C. for 2 hours. Incubation was completed by inactivation of the enzyme (90° C. for 30 s), followed by liquid-solid separation in a decanter.

The liquid so obtained was filtered using a 1 μm filter, to remove aggregates/solids. Subsequently, the liquid was concentrated to ⅓ of the original volume by ultrafiltration using a 10 kDa PolyEtherSulfone membrane (Microdyn Nadir; UP010). Next, the retentate was diluted to the original volume with water and again concentrated to ⅓ of the original volume.

The retentate so obtained was concentrated by evaporation to increase the solid content, and then spray dried.

Table 1 shows the basic composition of the hydrolysed pectic polysaccharide isolate so obtained.

TABLE 1

| Carbohydrates | Protein | Lipids | Moisture | Ash | Raw fiber |
|---|---|---|---|---|---|
| 81 | 6 | 0.5 | 6.0 | 6.0 | 1.0 |

The monosaccharide composition of the isolate was determined using the analytical methods described in: Analytical Biochemistry Vol. 207, Issue 1, 1992, pg 176 (neutral sugar analysis) and in Mol. Nutr. Food Res., Vol 61, Issue 1, 2017, 1600243 (uronic acid analysis and molecular size distribution). Table 2 shows the results.

TABLE 2

| Rha | GalA | Ara | Gal | Glc | Man | Xyl |
|---|---|---|---|---|---|---|
| 17 | 23 | 33 | 20 | 4 | 0 | 1 |

Example 2

2 kg of dried apple pomace (protein 6.5-8%, carbohydrates 71% (sugars 11%, dietary fiber 60%), ash 1.0-1.5%, fat 3.0-4.0%.) was dissolved in 18 kg of water in a 25 L stainless steel container and placed in a water bath of 45° C. The mixture was stirred continuously in order to keep insoluble components in dispersion. 20 g of Pectinex™ Ultra Mash was added after the apple pomace dispersion had reached 45° C. Incubation was continued for 2 hours. After these 2 hours the container was placed in an ice bath. Next, the dispersion was filled in centrifuge buckets and centrifuged for 5 min at 6000 g. The supernatants were collected in a 25 L stainless steel container after filtration over a 10 μm filter. The container was placed in a water bath of 98° C. After the dispersion had reached a temperature of 90° C., the mixture was heated for another 10 min in order to inactivate the enzyme. Next. the mixture was cooled down to 50° C. by placing the container in an ice bath.

The pH of the mixture was set to pH 5.0 by adding a 33% (m/m) NaOH solution. Next, the mixture was concentrated by a factor 5 and washed with 200% of water over an ultra-filtration membrane using a LAB20 set-up equipped with 10 kDa PolyEtherSulfone membrane (Microdyn Nadir; UP010) at 50° C. After ultra-filtration/diafiltration the isolate was freeze-dried using a lab-scale freeze dryer.

The monosaccharide composition of the isolate is shown in Table 3.

TABLE 3

| Rha | GalA | Ara | Gal | Glc | Man | Xyl |
|---|---|---|---|---|---|---|
| 8 | 18 | 48 | 9 | 10 | 0 | 6 |

Example 3

The dried carrot pomace of Example 1 was dispersed in demineralised water (100 g/l) and subjected to enzymatic hydrolysis on labscale using 3 different enzymolysis conditions:
1. Pectinex® Yield Mash ex Novozymes (0.2% w/w of total dispersion)
2. Pectinex® Ultra Mash ex Novozymes (0.2% w/w of total dispersion)
3. Pectinex® Ultra Mash ex Novozymes (0.05% w/w of total dispersion)

Enzymolysis (45° C., 120 minutes) was terminated by heating at 90° C. for 10 min, followed by centrifugation and extensive dialysis of the supernatant using a 10 kDa PolyEtherSulfone membrane (Microdyn Nadir; UP010).

A reference isolate was produced by introducing the dried carrot pomace in water (100 g/1), keeping the solution for 120 minutes at a temperature of 90° C., centrifugation, and dialysis of the supernatant by means of dialysis in the same way as the enzymolysed dispersions.

Example 4

The monosaccharide composition of the non-hydrolysed carrot RG-I polysaccharide of Example 3 (Reference) and of the enzymatically hydrolysed carrot RG-1 polysaccharide of Example 3 (Samples 1 to 3) was determined in the same way as in Example 1

The results of the monosaccharide analysis are shown in Table 4 (Rha=rhamnose; GalA=galacturonic acid; Ara=arabinose; Gal=galactose.

TABLE 4

| Sample | Mol. % Rha | Mol. % GalA | Mol. % Ara | Mol. % Gal | [GalA]:[Rha] | [Gal]:[Rha] | [Ara]:[Rha] |
|---|---|---|---|---|---|---|---|
| Reference | 6 | 62 | 14 | 16 | 10.3 | 2.7 | 2.3 |
| 1 | 10 | 45 | 19 | 23 | 4.6 | 2.3 | 2.0 |
| 2 | 17 | 35 | 28 | 16 | 2.1 | 1.0 | 1.6 |
| 3 | 13 | 47 | 23 | 15 | 3.7 | 1.2 | 1.8 |

Example 5

The immunomodulating activity of the non-hydrolysed carrot RG-I polysaccharides of Example 3 (Reference) and of the enzymatically hydrolysed carrot RG-I polysaccharides of Example 3 (Samples 1 to 3) was determined using a human peripheral blood mononuclear cells (PBMC) assay. Immuno Modulation Assay.

To assess the effect of the polysaccharide materials on immune function they were incubated with freshly isolated Peripheral Blood Mononuclear Cells (PBMC). In brief, PBMC were isolated from buffy coats of blood using Ficoll-plaque (Amersham). PBMC (2*10E6 cells/mL) were incubated in RPMI medium (Gibco™ RPMI 1640 Medium) with 300 μg RG-I polysaccharides for 20 hr (5% $CO_2$, 37° C.). Subsequently, supernatants were harvested and cytokines were measured using a bead array (CBA human inflammation kit, BD-Bioscience) measured on a flowcytometer (BD FACSCANTO II) according to the manufacturer's instructions. RPMI was used as negative control and LPS (from *E. coli*—Sigma L3012-5mG) as reference to which the results were normalized with LPS as 100%. Data are expressed as % normalized to the response induced by LPS, averaged over 3 different donors for 4 different cytokines and their sum.

Table 5 shows the results of the immunomodulation assay

TABLE 5

| Sample | TNF | IL10 | IL6 | IL1B | Sum |
|---|---|---|---|---|---|
| Reference | 23 | 6 | 22 | 17 | 69 |
| 1 | 200 | 68 | 91 | 81 | 441 |
| 2 | 367 | 106 | 142 | 214 | 828 |
| 3 | 435 | 124 | 124 | 150 | 832 |

Example 6

Hydrolysed pectic polysaccharide isolates were prepared from different sources, with and without pectinase treatment. Powders obtained by grinding and drying of bell pepper, carrot pomace, apple pomace, citrus pulp, sugar beet pulp, bilberry pomace, red grape pomace, white grape pomace, chicory pulp, olive pits and olive cake were dispersed in demineralised water (100 g/L) and subjected to enzymatic hydrolysis on labscale using Rapidase C600 (an enzyme mix containing pectin lyase, polygalacturonase, pectin esterase, cellulase and hemicellulase activity, Militz, H. Wood Sci. Technol. (1993) 28: 9) with enzyme concentration at 1 g/100 mL of total dispersion, at 45° C., for 120 minutes.

Enzymolysis was terminated by heating at 100° C. for 10 min, followed by centrifugation (18.000 g, 10 min) and extensive dialysis of the supernatant using a membrane with a 12-14 kDa (Visking, London, UK) cut off.

Reference isolates were produced by introducing the dry powders in water (100 g/L), keeping the solution for 120 minutes at a temperature of 90° C., centrifugation, and dialysis of the supernatant by means of dialysis in the same way as the enzymolysed dispersions.

The immunomodulating activity of the isolates produced with and without pectinase treatment was determined using human peripheral blood mononuclear cells (PBMC) assay at a concentration of 300 microg/mL as described for Example 3.

Table 6 shows the results of the immunomodulation assay

TABLE 6

| Source | Enzyme | TNF | IL10 | IL6 | IL1B | Sum |
|---|---|---|---|---|---|---|
| Bell pepper | No | 53 | 19 | 67 | 80 | 219 |
| | Yes | 90 | 21 | 75 | 89 | 275 |
| Carrot | No | 23 | 6 | 22 | 38 | 89 |
| | Yes | 480 | 58 | 85 | 132 | 755 |
| Apple pomace | No | 15 | 8 | 21 | 13 | 57 |
| | Yes | 70 | 26 | 64 | 42 | 202 |
| Citrus pulp | No | 0 | 1 | 4 | 17 | 22 |
| | Yes | 181 | 37 | 87 | 123 | 428 |
| Sugar beet pulp | No | 0 | 0 | 0 | 3 | 3 |
| | Yes | 4 | 2 | 7 | 20 | 33 |
| Bilbery pomace | No | 0 | 0 | 2 | 10 | 12 |
| | Yes | 2 | 1 | 6 | 14 | 23 |
| Red grape | No | 43 | 17 | 47 | 22 | 129 |
| | Yes | 167 | 54 | 106 | 88 | 415 |
| White grape | No | 100 | 20 | 61 | 34 | 215 |
| | Yes | 108 | 49 | 79 | 51 | 287 |
| Olive pit | No | 83 | 55 | 86 | 50 | 274 |
| | Yes | 162 | 87 | 108 | 91 | 448 |
| Olive cake | No | 51 | 9 | 49 | 19 | 128 |
| | Yes | 87 | 29 | 77 | 34 | 227 |
| Chicory pulp | No | 24 | 8 | 38 | 12 | 82 |
| | Yes | 128 | 62 | 94 | 73 | 357 |

The results of the monosaccharide analysis are shown in Table 7 (Rha=rhamnose; GalA=galacturonic acid; Ara=arabinose; Gal=galactose.

TABLE 7

| Source | Enzyme | Mol % Rha | Mol % GalA | Mol % ArA | Mol % Gal | [GalA]:[Rha] | [Gal]:[Rha] | [Ara]:[Rha] |
|---|---|---|---|---|---|---|---|---|
| Bell pepper | No | 6 | 71 | 8 | 7 | 12.1 | 1.3 | 1.3 |
| | Yes | 11 | 46 | 8 | 13 | 4.3 | 1.2 | 0.7 |
| Carrot | No | 6 | 62 | 14 | 16 | 10.6 | 2.8 | 2.4 |
| | Yes | 14 | 47 | 13 | 18 | 3.4 | 1.3 | 1.0 |
| Apple pomace | No | 2 | 31 | 33 | 11 | 19.9 | 6.7 | 21.1 |
| | Yes | 8 | 14 | 46 | 10 | 1.8 | 1.3 | 6.0 |
| Citrus pulp | No | 4 | 39 | 32 | 13 | 9.9 | 3.3 | 8.2 |
| | Yes | 8 | 30 | 37 | 10 | 3.9 | 1.3 | 4.9 |
| Sugar beet pulp | No | 4 | 54 | 32 | 7 | 13.1 | 1.8 | 7.8 |
| | Yes | 8 | 39 | 36 | 11 | 4.7 | 1.3 | 4.4 |
| Bilbery pomace | No | 3 | 75 | 8 | 6 | 26.8 | 2.3 | 2.7 |
| | Yes | 15 | 35 | 20 | 11 | 2.4 | 0.8 | 1.3 |
| Red grape | No | 7 | 32 | 24 | 15 | 4.8 | 2.3 | 3.6 |
| | Yes | 8 | 19 | 15 | 19 | 2.2 | 2.2 | 1.7 |
| White grape | No | 7 | 48 | 15 | 14 | 6.8 | 1.9 | 2.1 |
| | Yes | 8 | 39 | 11 | 16 | 4.7 | 1.9 | 1.4 |
| Olive pit | No | 3 | 30 | 14 | 5 | 8.9 | 1.6 | 4.2 |
| | Yes | 8 | 31 | 8 | 9 | 4.1 | 1.1 | 1.1 |
| Olive cake | No | 8 | 25 | 29 | 9 | 3.2 | 1.1 | 3.7 |
| | Yes | 11 | 29 | 24 | 12 | 2.7 | 1.1 | 2.2 |
| Chicory pulp | No | 1 | 68 | 19 | 5 | 68.0 | 5.0 | 19.0 |
| | Yes | 8 | 35 | 48 | 8 | 4.4 | 1.1 | 6.0 |

Example 7

Example 3 was repeated on different scales, i.e. at 20 liters (sample 1), 5,000 liters (sample 2) and 10,000 litres (sample 3), using the enzyme Pectinex® Ultra Mash ex Novozymes (conditions: 0.1% w/w of total dispersion, 45° C., 2 hrs, enzyme inactivation: 90° C. for 10 min). In samples 2 and 3, instead of centrifugation, decanting was used to separate the solids from the liquid. The supernatant was subjected to ultrafiltration, using a 10 kDa membrane, to remove small molecular components.

The monosaccharide composition of the hydrolysed polysaccharide materials was analysed in the same way as in Example 1.

The results of the analyses are shown in Table 8.

TABLE 8

| Sample | Mol. % Rha | Mol. % GalA | Mol. % Ara | Mol. % Gal | [GalA]:[Rha] | [Gal]:[Rha] | [Ara]:[Rha] |
|---|---|---|---|---|---|---|---|
| 1 | 17 | 28 | 30 | 22 | 1.6 | 1.3 | 1.7 |
| 2 | 17 | 23 | 33 | 20 | 1.4 | 1.2 | 2.0 |
| 3 | 15 | 28 | 29 | 19 | 1.8 | 1.2 | 1.9 |

The degree of acetylation and methylation was determined as follows: Polysaccharide samples (2-5 mg) were treated with sodium hydroxide (0.1 M, overnight, 20° C.). Released methanol was measured using head-space GC equipped with a DB-WAX ETR column, Cryo Focus-4 cold trap and FID detection (adapted from Huisman et al., Food Hydrocolloids, 18, 4, 2004, 665-668)

The samples were neutralized (1M HCl) and then the released acetyl was quantified using HPLC equipped with an Aminex HPX 87H column with guard column and RI detection (adapted from Voragen et al. Food Hydrocolloids, 1, 1, 1986, 65-70). Degree of esterification is expressed as molar amount of methanol and acetic acid released as percentage of the amount of uronic acid.

The results of the degree of esterification analyses are shown in Table 9.

TABLE 9

| | DM % [1] | DA % [2] | DA:DM |
|---|---|---|---|
| 2 | 16 | 42 | 2.6 |
| 3 | 21 | 36 | 1.7 |

[1] degree of methylation
[2] degree of acetylation

Example 8

The immunomodulating activity of the enzymatically hydrolysed carrot RG-I polysaccharides of Example 7 (Samples 1 to 3) was determined using a human peripheral blood mononuclear cells (PBMC) assay as described for Example 5. The results are shown in table 10.

TABLE 10

| | TNF | IL10 | IL6 | IL1B | Sum |
|---|---|---|---|---|---|
| 1 | 131 | 61 | 105 | 72 | 368 |
| 2 | 181 | 70 | 124 | 136 | 511 |
| 3 | 107 | 35 | 97 | 72 | 311 |

Example 9

The hydrolysed polysaccharide material of sample 2 of Example 7 was further hydrolysed, followed by isolation of a high molecular weight fraction. The polysaccharide material was dissolved in demineralised water (100 g/l) and subjected to further enzymatic hydrolysis (Pectinex® Ultra Mash ex Novozymes, 45° C., 14 hours). Enzymolysis was terminated by heating to 90° C. for 10 min.

A portion of the enzymolysed polysaccharide solutions was subjected to fractionation using semi-preparative size-exclusion chromatography to produce a fraction containing polysaccharides having a molecular weight of more than 70 kDa.

The monosaccharide composition of the non-fractionated hydrolysed polysaccharide and of the isolated high molecular fraction was analysed in the same way as in Example 1.

The results of the analyses are shown in Table 11.

TABLE 11

| | Mol. % Rha | Mol. % GalA | Mol. % Ara | Mol. % Gal | [GalA]:[Rha] | Ara:Rha | GaL:Rha |
|---|---|---|---|---|---|---|---|
| Non fractionated | 23 | 31 | 14 | 19 | 1.3 | 0.6 | 0.8 |
| >70 kDa | 15 | 23 | 17 | 38 | 1.5 | 1.1 | 2.5 |

The immunomodulating activity of the enzymolysed polysaccharide and the high molecular fraction thereof was determined using the methodology described in Example 5. The results are shown in Table 12.

TABLE 12

| 14 hrs enzymolysis | TNF | IL10 | IL6 | IL1B | Sum of All |
|---|---|---|---|---|---|
| Non-fractionated | 295 | 95 | 130 | 158 | 678 |
| >70 kDa fraction | 302 | 112 | 139 | 174 | 726 |

Example 10

Dried and milled pea hulls powder (ex Cosucra, Warcoing, Belgium) was dispersed in demineralised water (100 g/L) and subjected to enzymatic pre-hydrolysis with a thermostable alpha-amylase (Megazyme) at 90° C. for 30 min and further hydrolysis using pectinase (2 hr 45° C., 0.2 v/v % Pectinex® Ultra Mash, Novozymes). Enzymolysis was terminated by heating at 100° C. for 10 min, followed by centrifugation (18.000 g, 10 min) and extensive dialysis of the supernatant using a membrane with a 12-14 kDa (Visking, London, UK) cut off. The material was then lyophilized.

Milled sugar beet pulp powder (ex Suiker Unie, Dinteloord, NL) was processed in the same way as the pea powder, except that this the α-amylase pre-incubation step was omitted.

The monosaccharide composition of the isolates was determined using the same method as in Example 1. The results are shown in Table 13.

TABLE 13

| Sample | Mol. % Rha | Mol. % GalA | Mol. % Ara | Mol. % Gal | [GalA]:[Rha] | [Gal]:[Rha] | [Ara]:[Rha] |
|---|---|---|---|---|---|---|---|
| Pea | 8 | 57 | 14 | 6 | 7.1 | 1.8 | 0.8 |
| Sugar beet | 7 | 40 | 45 | 7 | 5.7 | 6.4 | 1.0 |

Example 11

Hydrolysed pectic polysaccharide isolates were prepared by dispersing carrot pomace in water (100 g/L).

Sample 1 was extracted at 90° C. for 120 minutes without added enzyme (extract yield: 4.8%)

Sample 2 was extracted by adding Rapidase C600 (an enzyme mix containing pectin lyase, polygalacturonase, pectin esterase, cellulase and hemicellulase activity, Militz, H. Wood Sci. Technol. (1993) 28: 9) with enzyme concentration at 1 g/100 mL of total dispersion, at 45° C., for 120 minutes. Enzymolysis was terminated by heating at 100° C. for 10 min (extract yield: 5.6%)

Both samples were subsequently centrifuged (18.000 g, 10 min) and the supernatant was extensively dialysed using a membrane with a 12-14 kDa (Visking, London, UK) cut off. After ultra-filtration/diafiltration the isolate was freeze-dried using a lab-scale freeze dryer.

Figure 3:
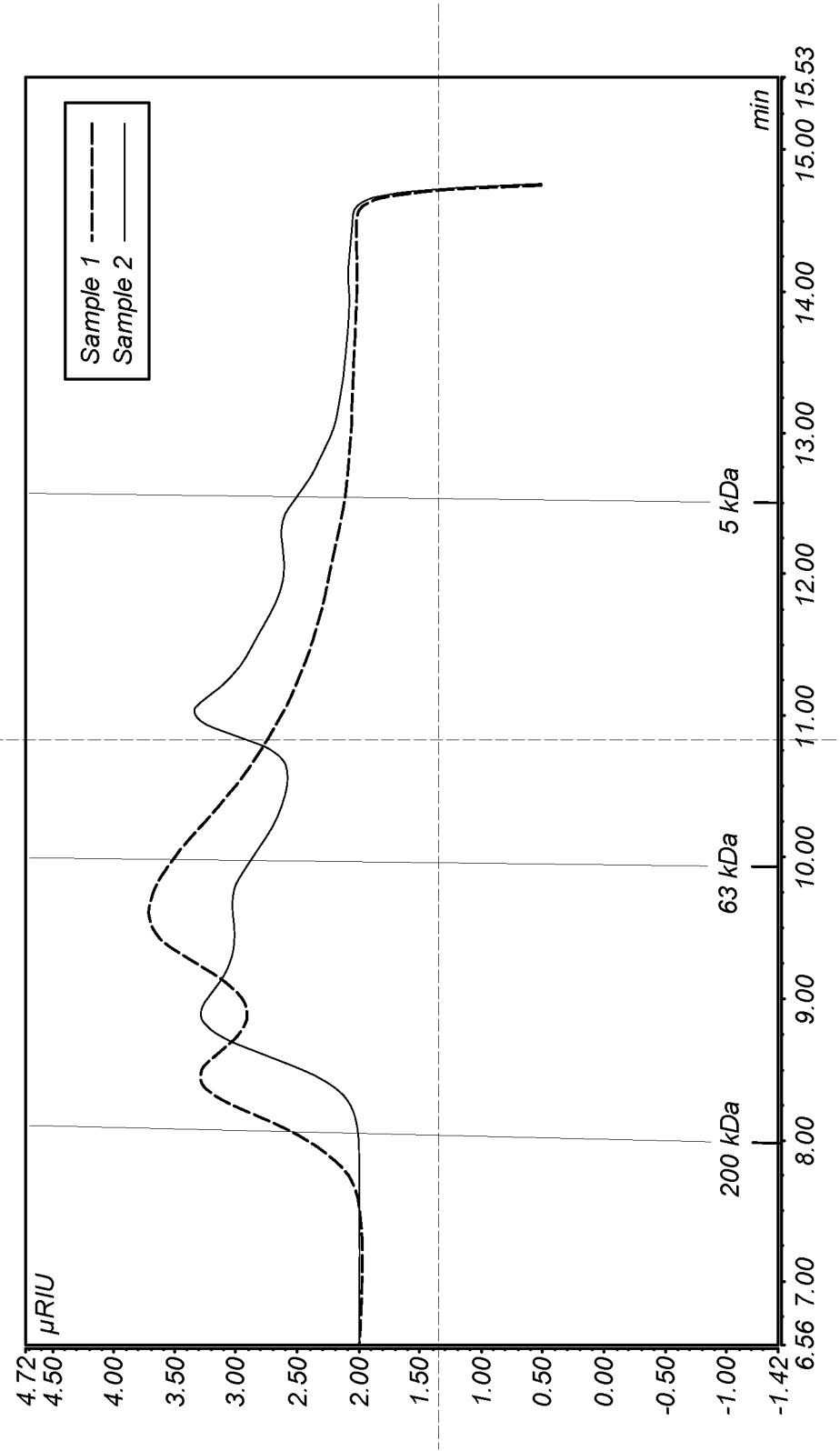
FIG. 3 shows the molecular size distribution of two hydrolysed pectic polysaccharide samples according to Example 11, as determined by HPSEC with refractive index detection.

The molecular size distribution of Sample 1 and Sample 2, as determined by HPSEC with refractive index detection, is shown in FIG. 3.

The monosaccharide composition of the two samples was analysed using the methodology described for Example 1. The results of the analyses are shown in Table 14.

TABLE 14

| | Mol. % Rha | Mol. % GalA | Mol. % Ara | Mol. % Gal | [GalA]:[Rha] | [Ara]:[Rha] | [Gal]:[Rha] |
|---|---|---|---|---|---|---|---|
| Sample 1 | 3.7 | 47.5 | 8.0 | 11.5 | 12.8 | 3.1 | 2.2 |
| Sample 2 | 8.4 | 34.7 | 7.3 | 12.2 | 4.1 | 1.5 | 0.9 |

The invention claimed is:

1. A method of producing a hydrolysed pectic polysaccharide isolate enriched in rhamnogalacturonan-I, the method comprising:
   (a) obtaining a pectin-rich substrate:
      (i) selected from pomace, aqueous extract of pomace, and combinations thereof,
      (ii) obtained from one or more crops selected from pear, carrot, and chicory without the use of organic solvent, and
      (iii) comprising at least 3% by weight of dry matter of pectic polysaccharides having a backbone consisting of galacturonic acid residues and rhamnose residues, the rhamnose residues being contained in a backbone consisting of galacturonic acid residues and rhamnose residues, said rhamnose residues being contained in alpha (1→4)-galacturonic-alpha (1→2)-rhamnose residues;
   (b) subjecting the pectin-rich substrate to enzymatic treatment, comprising one or more pectinases selected from pectin lyase (EC 4.2.2.10), pectate lyase (EC 4.2.2.2), endo-polygalacturonase (EC 3.2.1.15), exopolygalacturonase (EC 3.2.1.67 and EC 3.2.1.82) to partially hydrolyse the pectic polysaccharides;
   (c) subjecting an aqueous liquid containing the partially hydrolysed pectic polysaccharides to solid-liquid separation to produce a liquid fraction comprising partially hydrolysed pectic polysaccharides, the solid-liquid separation employing a solid-liquid separation technique selected from sedimentation, decanting, centrifugation, hydrocyclones, filtration, and combinations thereof;
   (d) subjecting the liquid fraction comprising the partially hydrolysed pectic polysaccharides to ultrafiltration using an ultrafiltration membrane having a molecular weight cut-off in the range of 5 to 100 kDa; and
   (e) recovering the ultrafiltration retentate, the recovered ultrafiltraton retentate containing galacturonic acid residues and rhamnose residues in a molar ratio of not more than 6:1.

2. The method according claim 1, wherein the pectin-rich substrate is selected from pomace.

3. The method according to claim 1, wherein the pectin isolate is obtained from chicory, and/or carrot.

4. The method according to claim 3, wherein the pectin isolate is obtained from carrot.

5. The method according to claim 1, wherein the pectin-rich substrate comprises at least 10-80% by weight of dry matter of cellulose material selected from cellulose, hemicellulose and combinations thereof.

6. The method according to claim 5, wherein at least 50 wt. % of the pectic polysaccharides present in the substrate does not dissolve in distilled water at 45° C. and pH 5.5 at a pectic polysaccharide concentration of 1 g/l.

7. The method according to claim 1, wherein the pectin-rich substrate is a pectin isolate comprising at least 10% by weight of dry matter of pectic polysaccharides.

8. The method according to claim 1, wherein the pectin-rich substrate subjected to enzymatic treatment is in the form of an aqueous liquid containing the pectin-rich substrate and having a dry matter content of 0.5-40 wt. %.

9. The method according to claim 1, wherein the enzymatic treatment is carried out at a pH in the range of 3.0 to 7.5.

10. The method according to claim 1, wherein the one or more pectinases are selected from pectin lyase (EC4.2.2.10) and pectate lyase (EC 4.2.2.2).

11. The method according to claim 1, wherein the one or more pectinases are selected from endopolygalacturonase (EC 3.2.1.15) and exopolygalacturonase (EC 3.2.1.67 and EC 3.2.1.82).

12. The method according to claim 1, wherein the enzymatic treatment comprises the use of one or more pectinesterases (EC 3.1.1.11) prior to or simultaneous with the partial hydrolysis using the one or more pectinases.

13. The method according to claim 1, wherein the ultrafiltration membrane has a molecular weight cut-off in the range of 6-50 kDa.

14. The method according to claim 1, further comprising drying the ultrafiltration retentate to a water content of less than 15 wt. %.

15. The method according to claim 1, wherein the recovered ultrafiltration retentate comprises pectic polysaccharides having a mass weighted average molecular weight of more than 20 kDa.

16. The method according to claim 15, wherein the recovered ultrafiltration retentate comprises pectic polysaccharides having a mass weighted average molecular weight of more than 30 kDa.

17. A method of producing a hydrolysed pectic polysaccharide isolate enriched in rhamnogalacturonan-I, the method comprising:
(a) obtaining a pectin-rich substrate:
  (i) selected from pomace, aqueous extract of pomace, and combinations thereof,
  (ii) obtained from one or more crops selected from apple, pear, carrot, and chicory without the use of organic solvent, and
  (iii) comprising at least 3% by weight of dry matter of pectic polysaccharides having a backbone consisting of galacturonic acid residues and rhamnose residues, the rhamnose residues being contained in a backbone consisting of galacturonic acid residues and rhamnose residues, said rhamnose residues being contained in alpha (1→4)-galacturonic-alpha (1→2)-rhamnose residues;
(b) subjecting the pectin-rich substrate to enzymatic treatment, comprising one or more pectinases selected from pectin lyase (EC 4.2.2.10), pectate lyase (EC 4.2.2.2), endo-polygalacturonase (EC 3.2.1.15), exopolygalacturonase (EC 3.2.1.67 and EC 3.2.1.82) to partially hydrolyse the pectic polysaccharides;
(c) subjecting an aqueous liquid containing the partially hydrolysed pectic polysaccharides to solid-liquid separation to produce a liquid fraction comprising partially hydrolysed pectic polysaccharides, said solid-liquid separation employing a solid-liquid separation technique selected from sedimentation, decanting, centrifugation, hydrocyclones, filtration, and combinations thereof;
(d) subjecting the liquid fraction comprising the partially hydrolysed pectic polysaccharides to ultrafiltration using an ultrafiltration membrane having a molecular weight cut-off in the range of 5 to 100 kDa; and
(e) recovering and drying the ultrafiltration retentate, the recovered ultrafiltration retentate preferably contains galacturonic acid residues and rhamnose residues in a molar ratio of not more than 6:1.

18. The method according to claim 1, further comprising adding the hydrolysed pectic polysaccharide isolate to a product selected from the group consisting of a nutritional formulation, a food product, a dietary supplement, a beverage, and a pharmaceutical product, in a concentration of at least 0.1% by weight of the dry matter that is contained in the product.

* * * * *